United States Patent [19]

Wurtman et al.

[11] Patent Number: 4,673,689

[45] Date of Patent: Jun. 16, 1987

[54] METHOD AND COMPOSITION FOR ENHANCING THE EFFECT OF INDIRECT-ACTING SYMPATHOMIMETIC AMINES

[75] Inventors: Richard J. Wurtman, Boston; Timothy J. Maher, Milton, both of Mass.

[73] Assignee: Massachusetts Institute of Technology, Cambridge, Mass.

[21] Appl. No.: 845,141

[22] Filed: Mar. 27, 1986

Related U.S. Application Data

[62] Division of Ser. No. 780,054, Sep. 25, 1985, Pat. No. 4,598,094.

[51] Int. Cl.⁴ ............................................ A61K 31/195
[52] U.S. Cl. ..................................................... 514/561
[58] Field of Search ......................................... 514/561

Primary Examiner—Stanley J. Friedman
Attorney, Agent, or Firm—Paul J. Cook

[57] ABSTRACT

Tyrosine or a tyrosine precursor is administered concomitantly with an indirect-acting sympathomimetic amine drug to increase the level of norepinephrine that can be released in sympathetic neuron synapses.

2 Claims, No Drawings

METHOD AND COMPOSITION FOR ENHANCING THE EFFECT OF INDIRECT-ACTING SYMPATHOMIMETIC AMINES

This is a divisional of co-pending application Ser. No. 780,054 filed on Sept. 25, 1985, now U.S. Pat. No. 4,598,094.

BACKGROUND OF THE INVENTION

This invention relates to a method and composition for enhancing the desirable effects of drugs comprising indirect-acting sympathomimetic amines.

Indirect-acting sympathomimetic amines function by releasing stored norepinephrine from sympathetic nerve endings The major problem with their use is that after a few doses, they often stop functioning, i.e., tachyphylaxis sets in. Tachyphylaxis is known to be associated with partial depletion of the norepinephrine in the nerve endings, leading to the supposition that there are releasable and non-releasable pools of norepinephrine and that when the drugs cease functioning, it is because the releasable pools have been severely depleted.

Prior to the present invention, tyrosine or a tyrosine precursor has been administered concomitantly with a drug in order to enhance the effectiveness of the drug or to reduce or eliminate undesirable effects associated with the drug.

U.S. Pat. No. 4,224,343 discloses the administration of tyrosine or a tyrosine precursor concomitant with a drug which has the undesirable effect of increasing prolactin secretion, thereby to decrease prolactin secretion. Examples of such drugs are reserpine, aldomet and clonidine.

U.S. Pat. No. 4,271,192 discloses that tyrosine can be administered with drugs known to reduce the risk of ventricular fibrilation in order to potentiate the drugs' activity. Representative suitable drugs include procainamide, quinidine, propranolol and diphenylhydantoin.

U.S. Pat. No. 4,327,112 discloses the administration of tyrosine or a tyrosine precursor to a human together with a drug known to increase blood pressure in order to potentiate the dugus activity for increasing blood pressure. Typical drugs disclosed are neosynephrine, calcium chloride, ephedrine, dopamine and dorepinephrine.

U.S. Pat. No. 4,470,987 also discloses the use of the combination of tyrosine and a drug in order fo prevent ventricular fibrilation.

It would be desirable to provide a means for preventing tachyphylaxis with indirect-acting sympathomimetic amine drugs so that the drugs could be rendered useful for long periods.

SUMMARY OF THE INVENTION

The present invention provides a method and composition for preventing tachyphylaxis of indirect-acting sympathomimetic amine drugs. Tyrosine or a tyrosine precursor is administered concomitantly with the drug and the tyrosine is converted to norepinephrine in a form which renders it releasable in sympathetic nerve synapses. The result of utilizing tyrosine prevents tachyphylaxis of the drug.

DETAILED DESCRIPTION OF SPECIFIC EMBODIMENTS

In accordance with this invention, tyrosine or a tyrosine precursor such as phenylalanine is administered concomitnatly with an indirect-acting sympathomimetic amine drug, thereby to increase the level of norepinephrine which can be released in sympathetic neuron synapses.

Representative indirect-acting sympathomimetic amine drugs which can be utilized in the present invention include ephedrine, metaraminol, hydroxyamphetamine or mephentermine which are normally administered intravenously; pseudoephedrine, phenylpropanolamine, amphetamine, or methoxyphenamine which are administered orally or by inhalation or oxymetazoline, propylhexedrine, tuaminoheptane, naphazoline, tetrahydrozoline, xylometazoline or cyclopentamine which are administered nasally. These drugs are administered to a human patient at the normally preferred dosage levels which are readily available to the practitioner in this art. For example, ephedrine is administered intravenously at dosages between about 2 and about 60 mg, while pseudoephedrine orally is administered at dosages between about 10 and 200 mg.

The amount of tyrosine or tyrosine precursor such as phenylalanine administered is between about 2 and 200 mg/kg body weight/day, preferably between about 10 and 100 mg/kg body weight/day in order to obtain tyrosine blood plasma concentrations between about 15 and 100 $\mu$g/ml, preferably between about 20 and 40 $\mu$g/ml, thereby to obtain a blood level of tyrosine which prevents tachyphylaxis of the indirect-acting sympathomimetic amine drug. When the tyrosine or tyrosine precursor is administered in a liquid carrier such as saline or sugar solution, the concentration of tyrosine or tyrosine precursor should be between about 5 $\mu$g/ml and 100 $\mu$g/ml. The tyrosine can be administered orally, parenterally or enterally.

The tyrosine or tyrosine precursor can be administered as free amino acids, esters, salts, natural or synthetic polymers or constituents of food. The route of administration can be oral or parenteral, e.g. intravenous.

The following example illustrates the present invention and is not intended to limit the same.

EXAMPLE I

This example illustrates that an animal administered tyramine, an indirect-acting sympathomimetic amine drug, can be treated to prevent tachyphylaxis of the tyramine by adding tyrosine to the perfusion solution, the effect of tyramine to accelerate heart rate was maintained, while, in untreated rats, heart rate changes were not sustained with repeated tyramine administrations. Isolated beating rat hearts are perfused with a standard solution (Chenoweth-Koelle solution). At intervals, tyramine is added to the perfusate and the increase in heart rate is measured (peak response). As shown in the control experiment, in the absence of tyrosine, tyramine elicits a 93.4% increase in heart rate, but the second tyramine dose fails to elicit a significant heart rate increase at all. When tyrosine is present in the medium the maximum increase in heart rate elicited in the initial tyramine dose is increased (from 93.4 to 242%, with 50 M tyrosine or to 156.2% with 6.25 M tyrosine), and subsequent tyramine doses-up to the 6th test- continued to function as desired. The results are shown in the following tables:

EFFECT OF L-TYROSINE ON THE CHRONOTROPIC RESPONSE OF THE ISOLATED RAT HEART

TABLE I

| Control (Chenoweth-Koelle solution) | |
|---|---|
| Tyramine Dose Number* | Percent Increase in Heart Rate Mean ± S.E.M. |
| 1 | 93.4 ± 7.7 |
| 2 | 0 |
| L-Tyrosine (50 μM) | n = 9 |

*350 μMol Tyramine Hydrochloride is administered at ten-minute intervals for sixty minutes.

TABLE II

| Tyramine Dose Number* | Percent Increase in Heart Rate Mean ± S.E.M. |
|---|---|
| 1 | 242.2 ± 20.0 |
| 2 | 202.0 ± 22.2 |
| 3 | 143.9 ± 9.6 |
| 4 | 134.6 ± 4.1 |
| 5 | 128.3 ± 3.6 |
| 6 | 129.0 ± 2.9 |
| L-Tyrosine (25 μM) | n = 8 |

*350 μMol Tyramine Hydrochloride is administered at ten-minute intervals for sixty minutes.

TABLE III

| Tyramine Dose Number* | Percent Increase in Heart Rate Mean ± S.E.M. |
|---|---|
| 1 | 169.0 ± 10.8 |
| 2 | 126.3 ± 13.1 |
| 3 | 115.0 ± 12.0 |
| 4 | 118.5 ± 8.0 |
| 5 | 112.5 ± 9.3 |
| 6 | 106.8 ± 5.0 |

TABLE III-continued

| Tyramine Dose Number* | Percent Increase in Heart Rate Mean ± S.E.M. |
|---|---|
| L-Tryosine (12.5 μM) | n = 3 |

*350 μMol Tyramine Hydrochloride is administered at ten-minute intervals for sixty minutes.

TABLE IV

| Tyramine Dose Number* | Percent Increase in Heart Rate Mean ± S.E.M. |
|---|---|
| 1 | 159.7 ± 14.6 |
| 2 | 149.3 ± 1.4 |
| 3 | 138.7 ± 6.1 |
| 4 | 138.7 ± 11.1 |
| 5 | 139.0 ± 12.2 |
| 6 | 131.0 ± 5.7 |
| L-Tyrosine (6.25 μM) | n = 5 |

*350 μMol Tyramine Hydrochloride is administered at ten-minute intervals for sixty minutes.

TABLE V

| Tyramine Dose Number* | Percent Increase in Heart Rate Mean ± S.E.M. |
|---|---|
| 1 | 156.2 ± 6.8 |
| 2 | 132.0 ± 8.3 |
| 3 | 118.4 ± 6.9 |
| 4 | 119.2 ± 7.1 |
| 5 | 115.6 ± 7.4 |
| 6 | 116.8 ± 7.2 |

*350 μMol Tyramine Hydrochloride is administered at ten-minute intervals for sixty minutes.

We claim:
1. The process for preventing tachyphylaxis of phenylpropanolamine which comprises administering to a patient concomitantly with said phenylpropanolamine a catecholamine precursor selected from the group consisting of tyrosine, a tyrosine precursor or a mixture of tyrosine and a tyrosine precursor to obtain a tyrosine blood plasma concentration between about 15 and 100 μg/ml.
2. The process of claim 1 wherein said catocholamine precursor is tyrosine.

* * * * *